United States Patent [19]

Kai et al.

[11] Patent Number: 5,378,630
[45] Date of Patent: Jan. 3, 1995

[54] TEST STRIP AUTOMATIC SUPPLY DEVICE AND ANALYTICAL INSTRUMENT USING THE SAME

[75] Inventors: Susumu Kai; Isao Shindo, both of Katsuta; Shigeo Mutoh, Hitachiota; Kasumi Yoshida, Mito, all of Japan

[73] Assignees: Hitachi, Ltd.; Hitachi Instrument Engineering Co., Ltd., both of Japan

[21] Appl. No.: 974,273

[22] Filed: Nov. 10, 1992

[30] Foreign Application Priority Data

Nov. 14, 1991 [JP] Japan ................. 3-298785

[51] Int. Cl.⁶ .................. G01N 35/00; B65H 3/00
[52] U.S. Cl. ...................... 436/43; 221/272; 422/63; 422/99
[58] Field of Search .......... 422/63, 67, 99, 58; 436/43; 221/268, 272

[56] References Cited

U.S. PATENT DOCUMENTS

| | | |
|---|---|---|
| 1,750,315 | 3/1930 | Franks et al. ............ 198/400 |
| 2,689,667 | 9/1954 | Thompson ............. 221/170 |
| 4,218,421 | 8/1980 | Mack ..................... 422/66 |
| 4,453,406 | 6/1984 | Spitzer ................. 73/866.5 |
| 4,710,351 | 12/1987 | Wogoman .............. 422/50 |
| 4,777,907 | 10/1988 | Sanger . |
| 4,796,744 | 1/1989 | Sanger . |
| 4,876,204 | 10/1989 | Inoue et al. ............ 436/46 |
| 4,965,983 | 10/1990 | Muller et al. ........... 53/435 |
| 4,972,935 | 11/1990 | Gross et al. ............ 198/395 |
| 5,097,938 | 3/1992 | Gruner et al. .......... 198/397 |

FOREIGN PATENT DOCUMENTS

| | | |
|---|---|---|
| 255070 | 3/1988 | European Pat. Off. . |
| 449100 | 2/1991 | European Pat. Off. . |
| 61-91571 | 5/1986 | Japan . |
| 1602195 | 11/1981 | United Kingdom . |

*Primary Examiner*—Robert J. Warden
*Assistant Examiner*—Robert Carpenter
*Attorney, Agent, or Firm*—Fay, Sharpe, Beall, Fagan, Minnich & McKee

[57] ABSTRACT

A test strip automatic supply device has: a cylindrical container 11 provided with a slit 15 which is formed in a side wall thereof so as to contain an elongate test strip; a container-supporting table having, in an upper portion thereof, a semi-cylindrical concave surface provided with an opening 20 which is formed in a middle portion of the concave surface so as to allow a test strip fitted in the slit of the container 11 to fall through and be taken out; and a carrying stage 31 which receives and transports a test strip falling from the slit 15. While the transporting stage 31 is transporting a test strip, an optical detector finds whether the test strip is faced up or down. The device has such a function that a side-reversing mechanism flips it over during transportation if it is face down. An operator only has to put test strips in the container. The tests strips are automatically let out of the container one at a time.

11 Claims, 6 Drawing Sheets

TEST STRIP AUTOMATIC SUPPLY DEVICE AND ANALYTICAL INSTRUMENT USING THE SAME

BACKGROUND OF THE INVENTION

1. Field of the Invention

The present invention relates to a test strip automatic supply device and an analytical instrument using the same and, more particularly, to a device and an instrument which are suitable for analysis of organic samples, such as urine or blood samples, by using test strips which contain reagents.

2. Description of the Related Art

Test strips are often used in clinical examinations in order to quickly perform different analyses on urine or blood samples. A test strip is composed of a narrow, long and flat strip made of, e.g., plastic, and a plurality of reagent sections which contain different reagents and are stuck to the strip.

A test strip automatic analytical instrument which automatically handles such test strips is disclosed in Japanese Patent Application Laid-Open No. 61-91571. In this known device, an arm having a test strip grip device is moved from a test strip automatic supply mechanism, via a sample table having sample containers into which test strips are dipped, to a photometer mechanism which optically analyzes the test strips having various developed colors. The test strip automatic supply mechanism supplies one test strip at a time to a position where the arm starts handling a test strip. The test strip automatic supply mechanism described in Japanese Patent Application Laid-Open No. 61-91571 has a hopper provided with a slidable bottom portion which moves to carry a test strip placed in the hopper to the outside.

Since the above test strip automatic supply mechanism described in Japanese Patent Application Laid-Open No. 61-91571 employs the above-described method, in which elongate test strips are supplied by slidingly moving the bottom portion of the hopper, test strips are likely to be stuck between the bottom portion and the wall of the hopper when the bottom portion moves to carry a test strip out of the hopper. Thus, this known device has a problem in that the smooth operation thereof may be interrupted.

SUMMARY OF THE INVENTION

Accordingly, an object of the present invention is to provide a test strip automatic supply device and a test strip analytical instrument in which test strips are automatically and smoothly supplied.

In a test strip automatic supply device according to the present invention, a barrel-shaped container is provided for containing a plurality of test strips, and a wall of this barrel-shaped container has a slit in which a test strip can be contained. The barrel-shaped container is reciprocally rotated back and forth so that one of the test strips is fitted into the slit. Then, while such rotation is stopped, the test strip in the slit is let out of the barrel-shaped container and placed at an external take-out position of the test strip automatic supply device.

The barrel-shaped test strip container has a test strip-containing chamber which has a depth corresponding to the lengths of test strips. A plurality of test strips are housed in the chamber in such an arrangement that the lengths of these test strips are parallel to one another. A wall of the barrel-shaped container has a slit which can contain the entire body of a test strip. A spill-out preventing member is provided near the outside periphery of the barrel-shaped container so as to cover at least a region within which the slit moves during rotation of the barrel-shaped container. The spill-out preventing member prevents a test strip from spilling out through the slit during rotation of the barrel-shaped container.

When the barrel-shaped container is reciprocally rotated back and forth, the test strips inside the barrel-shaped container move substantially perpendicularly to their lengths and, thus, one of the test strips slips into the slit, which is formed in the wall of the barrel-shaped container. To help a test strip unfailingly enter the slit, a test strip guide member should preferably be provided inside the barrel-shaped container. Such a guide member, for example, remotely covers the slit and has a shape such as to allow a test strip to reach the inside of the slit from one end side of the length of the slit and prevent a test strip from reaching the inside of the slit from the other end side.

When for and aft rotation of the barrel-shaped container is stopped so that the slit is positioned at the test strip let-out position, the test strip held in the inside of the slit is let out of the barrel-shaped container and transported to the external take-out position by transporting means. The test strip is supplied in such a manner that following operations to the test strip can be smoothly performed.

BRIEF DESCRIPTION OF THE DRAWINGS

FIG. 6 illustrates a test strip, FIG. 7 schematically illustrates the entire construction of an analytical instrument according to an embodiment of the present invention.

DETAILED DESCRIPTION OF THE PREFERRED EMBODIMENTS

Figure 6:
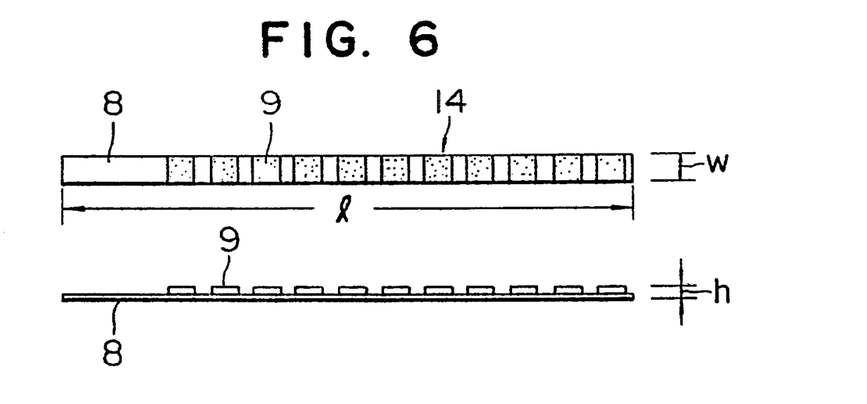

An example of a test strip is shown in FIG. 6. A test strip 14 is composed of an elongate plate-like plastic stick 8 having a length of l and a plurality of reagent sections 9 on the stick 8 which contain reagents. The test strip is dipped at the same time in a sample sufficiently deep so that all the reagent sections 9 are submerged, and then pulled up from the sample to let color development reactions progress. In general, a reagent section has a square size of about 5×5 mm and a thickness of 0.5 to 1.5 mm. The test strip 14 shown in FIG. 6 has a length l of 120 mm, a width w of 5 mm and a height h of 1.8 mm. The reagent sections 9 are formed of filter paper or felt.

The present invention may be applied to analysis of organic samples such as urine or blood samples. An automatic analytical instrument for urine samples according to an embodiment of the present invention will be described hereinafter.

Figure 7:
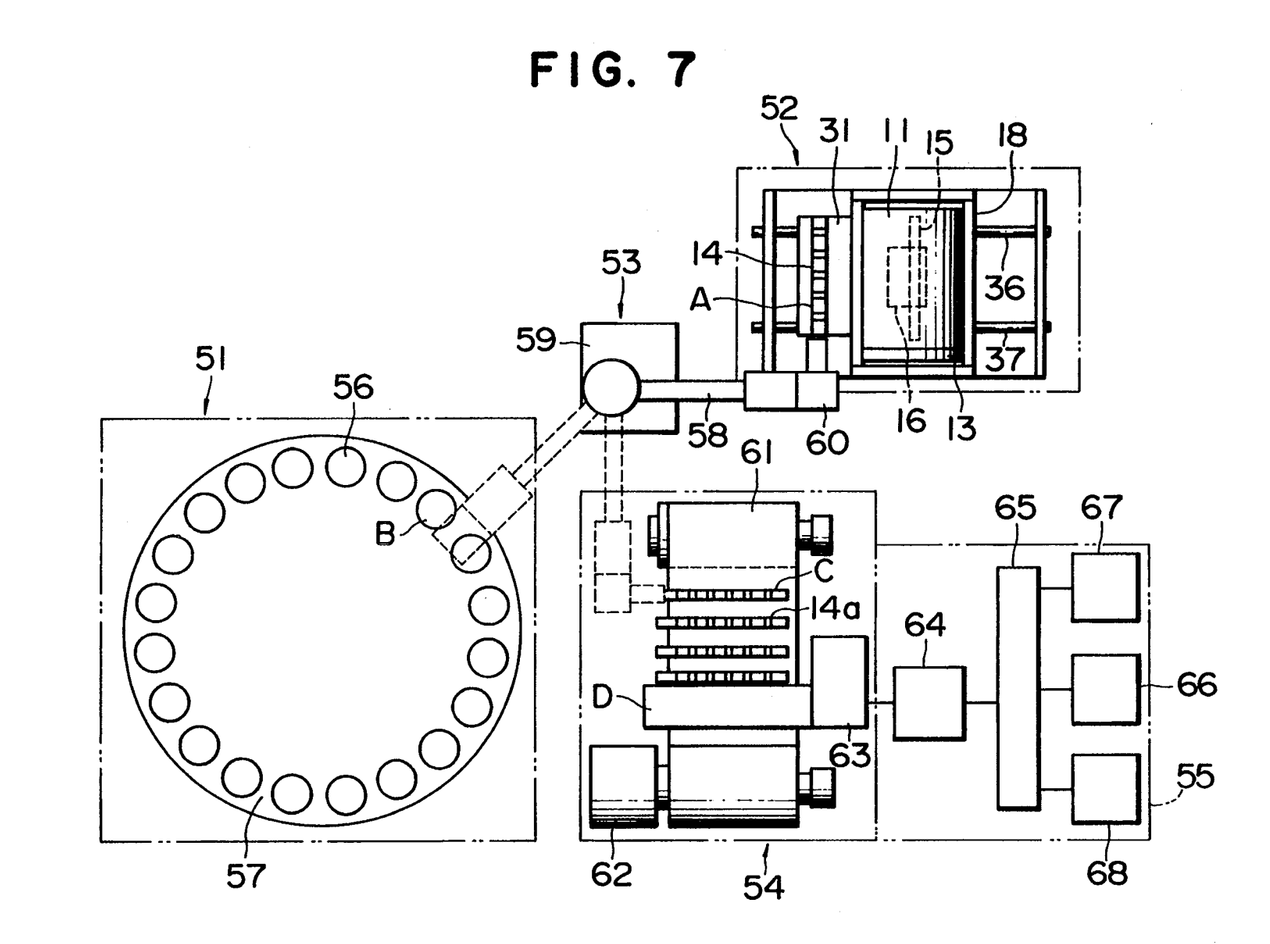
Figure 8:
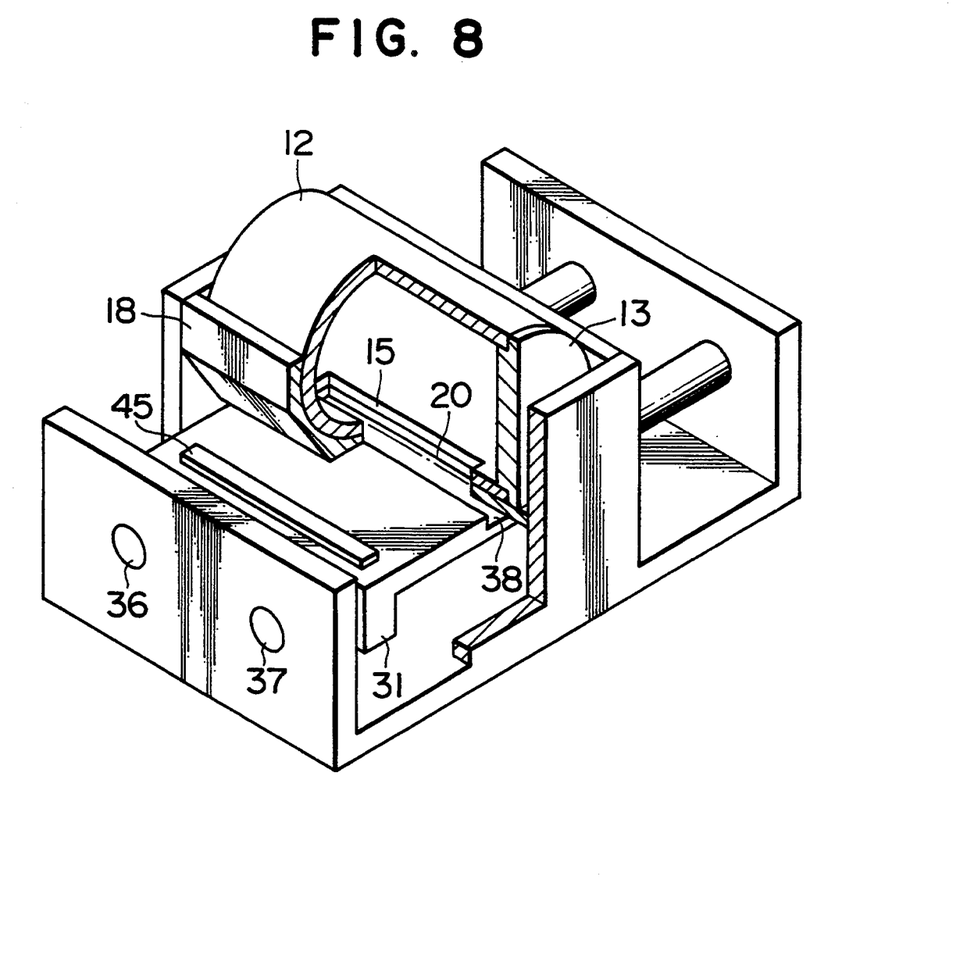
FIG. 8 is a partially broken external view of the device shown in FIG. 1.
Figure 9:
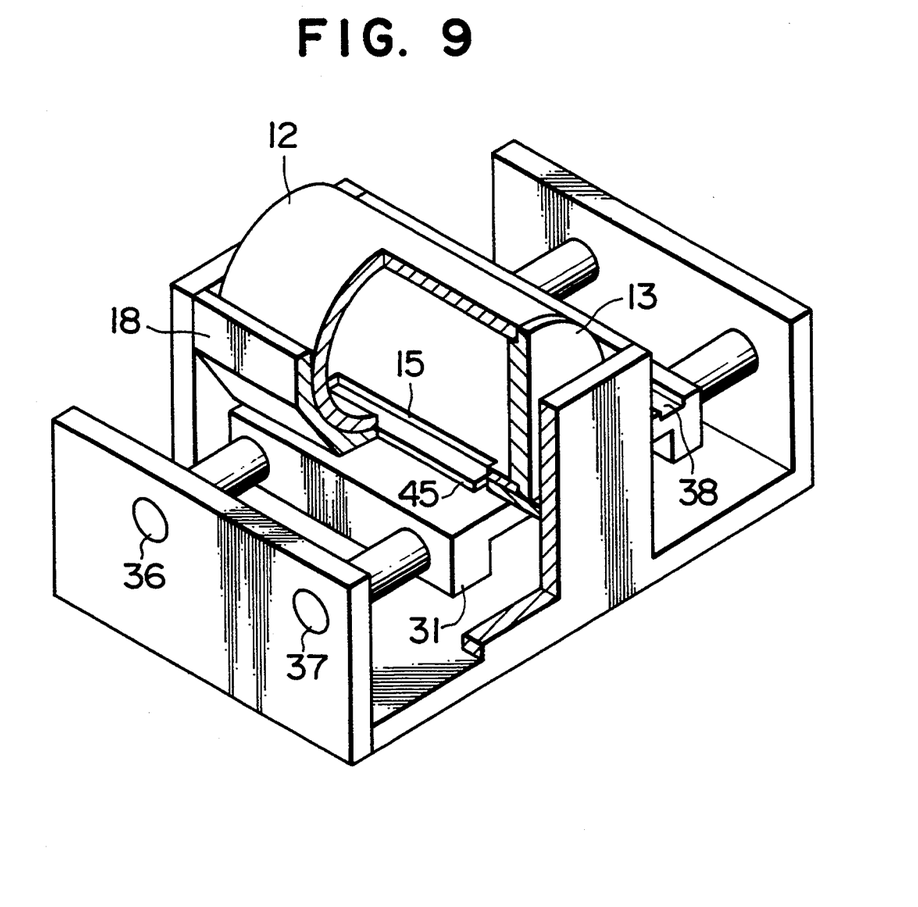
FIG. 9 is a partially broken external view of the device shown in FIG. 1 when the stage is moved.

FIG. 7 schematically illustrates the entire construction of an automatic analytical instrument for urine according to an embodiment of the present invention. Referring to FIG. 7, the analytical instrument comprises: a test strip automatic supply device 52, an autosampler 51, a test strip handling device 53, a measuring device 54, and a control and data processing device 55. The control and data processing device 55 controls the operations of the various devices and means, and processes measurement data of the reagent sections of the test strip, the data being obtained by a photometer 63, and outputs the results of measurement.

The autosampler 51 sequentially transports urine sample containers 56 arranged on a turntable 57 to a test strip dipping position B. The test strip automatic supply device 52 supplies one test strip at a time from a barrel-shaped container 11 containing many test strips, to a predetermined external take-out position A. Supplying of test strips to the external take-out position A is synchronized with the operational cycles of the analytical instrument.

One of the substantially flat sides corresponding to end plates of the barrel-shaped container 11 is provided with a closure 13 which allows test strips to be put in or taken out of the barrel-shaped container 11. A lowest portion of the curved wall of the barrel-shaped container 11 is provided with a slit 15. A guide member 16 is arranged so as to cover the slit 15. The guide member 16 helps a test strip unfailingly slip into the slit 15.

The barrel-shaped container 11 is slidably mounted on a container supporting table 18, which serves to prevent a test strip from spilling out and also to keep out the outside air. Under the container supporting table 18 is provided a test strip supporting stage 31 for transporting a test strip, which has been let out through the slit 15, to an external take-out position A. The test strip transporting stage 31 is movable on guide shafts 36, 37, and when it moves, the top surface of the transporting stage 31 slides on the bottom surface of the container supporting table 18.

The test strip handling device 53 comprises: a turnable arm 58, driving means 59, and a test strip grip device 60 provided on a front end portion of the arm 58. After a test strip is supplied to the external take-out position A, the test strip handling device 53 grips the test strip by using the grip device 60 and then transports it to the dipping position B, where the handling device 53 dips the test strip 14 held by the grip device 60 into a sample positioned at the dipping position B sufficiently deep so that all the reagent sections 9 of the test strip 14 are submerged. After dipping the test strip 14 for a certain length of time, the handling device 53 pulls the test strip 14 up from the sample and transports it to the measuring device 54, where the handling device 53 releases the test strip from the grip device 60 at a test strip mounting position C. Then, the handling device 53 moves so that the grip device 60 is back to the external take-out position A of the test strip automatic supply device 52. By this time, the next test strip has already been supplied to the external take-out position A. The above-described operation is repeated during analysis, The measuring device 54 uses a rolled paper 61 to convey test strips 14a received from the test strip handling device 53. The rolled paper 61 is wound up intermittently with time intervals of a certain length by winding means 62, thus conveying the test strips 14a from the mounting position C toward a photometry position D. A test strip 14a reaches the photometry position D a predetermined length of time after being dipped in the sample.

A photometer 63 comprises: a light source which emits light of wavelengths corresponding to the various analyses; and small reflection-type detectors having silicon photodiode light-receiving elements. These light reflection-type detectors are arranged in detection positions corresponding to the reagent sections of the test strips 14a, and measure the intensities of light reflected from the reagent sections which have colors developed.

The measurement data are sent through an A/D converter 64 to a control unit 65, which processes the data response to an input to an operating panel 68, which starts the analytical operation. The processed data are then displayed in a liquid crystal display 66 and printed out by a printer 67. Finally test strips which have been analyzed are rolled up together with the rolled paper 61 around the winding mechanism 62. When the analytical operation is finished, the rolled paper including these test strips is discarded.

The construction of the test strip automatic supply device 52 employed in the analytical instrument shown in FIG. 7 will be described with reference to FIGS. 1 to 5 and 8 and 9. These Figures show a cylindrical container as an example of the barrel-shaped container 11 which houses a plurality of test strips.

Figure 1:
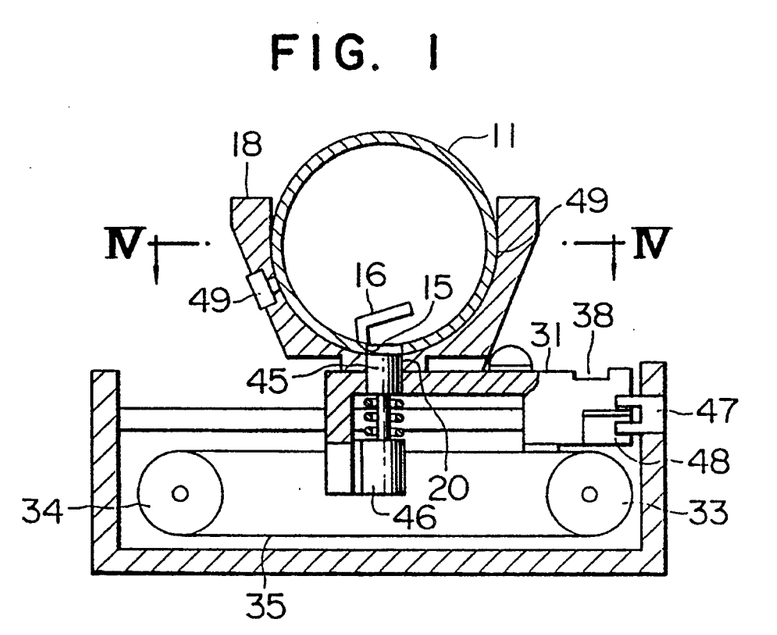
FIG. 1 is a longitudinal sectional view of the essential portions of a test strip automatic supply device according to the present invention.

A barrel-shaped container 11 comprises a container body 12 and a closure 13 which is provided with a drying agent chamber 17 containing a drying agent. A test strip housing chamber is formed between a side wall of the drying agent chamber 17 and the end (the relatively flat portion) of the container body 12. The distance therebetween, in other words, the depth of the test strip housing chamber, is slightly larger than the length l of a test strip 14. Because of this dimension, the test strips which are put in the housing chamber in such an arrangement that the lengths of the test strips are substantially parallel to one another will remain in such an arrangement even when the barrel-shaped container 11 is reciprocally rotated.

The curved wall of the barrel-shaped container 11 extends parallelly to the rotational axis and is provided with a substantially rectangular slit 15 which has such dimensions and a shape that a test strip substantially fits therein. More specifically, the slit 15 has a length slightly larger than the length l of a test strip 14, a width slightly larger than the width w of a test strip 14, and a depth substantially the same as the height h of a test strip 14. A guide member 16 is provided at the rotational-axis side of the slit 15. The guide member 16 extends over the slit 15 and has a leg portion which is fixed to the wall at the side of the slit 15. The leg portion allows a test strip approaching the slit 15, e.g., clockwise, to reach the slit 15, but prevents test strips which approach the slit 15, e.g., counterclockwise, from reaching the slit 15.

The clearance between an extending portion of the guide member 16 and the upper edge of the slit 15 is larger than the height h of a test strip 14 and smaller than twice the height h of the same (2 h). Thus, test strips smoothly enter the inside of the slit 15, one at a time.

The cylindrical container 11 is reciprocally rotated by a rotational driving means, a pulse motor 25. The rotational angle of the for and aft rotation of the container 11 (for and aft rotation about an axis at its center)

is controlled by a control unit based on signals generated by a partially-cut-away disc detecting means 29 which is mounted on a firmly fixed support table 18 and detects a partially-cut-away disc 30 connected to a rotational shaft 22 of a torque transmission mechanism. The rotational angle of for and aft rotation of the cylindrical container is 30° or greater both clockwise and counterclockwise. Such a rotational angle causes test strips in the container to easily move along the curved surface of the container.

The bottom portion of the cylindrical container 11 is engaged with a power transmitting projection 21 (see FIG. 4) of the torque transmission mechanism. On the other hand, the closure 13 of the container 11 is supported by a supporting shaft 24 which is provided with a pressing spring 23. Therefore, the container 11 can be easily taken out by pushing the container 11 to the left in FIG. 4 until the container body 12 is disengaged from the projection 21 and lifting the container 11. Though only one slit is formed in the container 11 in the Figures, two or more slits may be provided if necessary.

The outside longitudinal surface of the barrel-shape container 11 is formed so as to be slidable on the inside curved surface of a container-supporting table 18. This container-supporting table 18 prevents the slit 15 from coming outside during rotation of the container 11. If the slit 15 came outside, a test strip in the container 11 would spill out through the slit 15. Therefore, the container-supporting table 18 is arranged so as to cover the region within which the slit 15 rotationally moves during rotation of the container 11, thus serving as a test-strip spill-out preventing member.

In general, the reagent sections 9 of test strips are likely to be affected if exposed to moisture for a long time. Therefore, a drying agent is provided in the container 11 to keep the humidity in the container 11 at a low level. Further, to reduce ventilation through the slit 15, the container-supporting table 18 embraces the outer periphery of the container 11 so as to cover the entire region of movement of the slit 15.

The container-supporting table 18 also covers the outer peripheral surface of a lower portion of the container 11. In order to let a test strip out, a lower portion of the container-supporting table 18 is provided with an opening 20 in a position corresponding to the position to which the slit 15 comes when the container 11 stops rotating. Thus, the opening 20 leads a test strip from the slit 15 to the transporting stage 31. The opening 20 is kept closed by a shutter while the container 11 is rotating and is opened to let a strip fall from the slit 15 of the container 11 when the rotation thereof is stopped.

When a test strip falls, it is loaded on a test strip-receiving groove 38 formed on the test strip transporting stage 31, which is slidingly movable. The receiving groove 38 has a length and a width in accordance with those of the test strips.

Side wall members are provided on both sides of a member which forms a concave surface 19 of the container-supporting table 18. The side wall members support the torque transmission mechanism. The opening 20 is formed in a middle portion of the concave surface 19. The cylindrical test strip container 11 should preferably be made of a light-transmitting material such as acrylic resin. The container-supporting table 18 is formed so as to allow the container 11 to rotate to 90° both clockwise and counterclockwise. Further, the container-supporting table 18 is opened upward so as to allow the container 11 to be removed therefrom.

Figure 4:
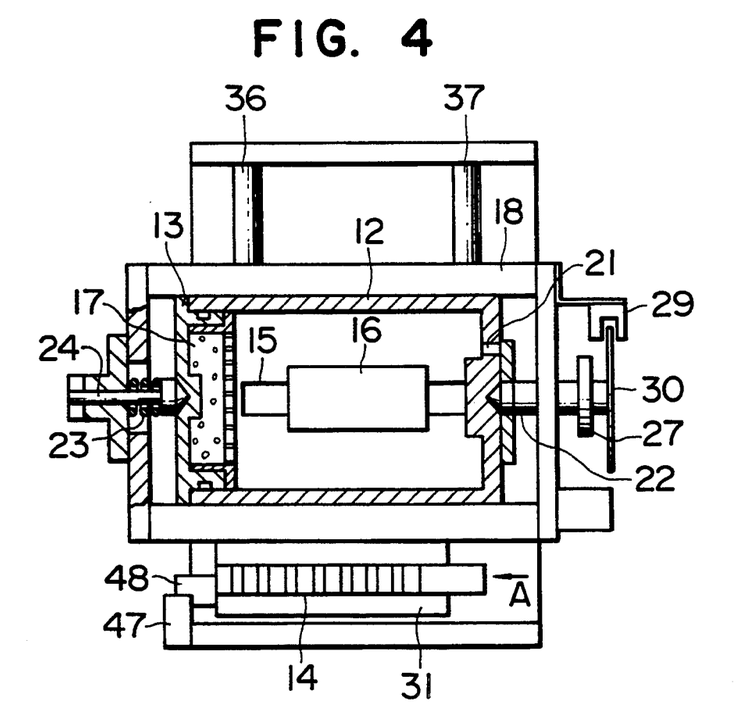
FIG. 4 is a sectional view taken along line IV—IV of FIG. 1.
Figure 5:
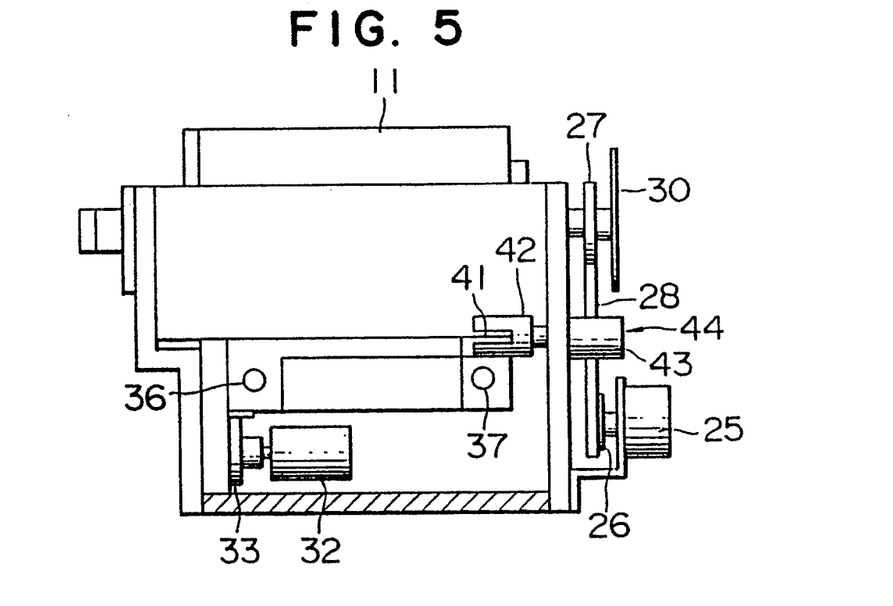
FIG. 5 is a front view of the device shown in FIG. 1.

The cylindrical container 11 is supported by a supporting shaft 22 provided with the projection for transmitting torque and by the movable shaft 24 provided with a spring 23 which axially presses the container 11. Torque is transmitted from the pulse motor 25 to the container 11, by way of pulleys 26, 27 and a timing belt 28. The rotational angle of the container 11 is controlled based on the detection performed by the detector 29 and the rotational disc 30 having a cut-away portion at the circumference.

The test strip transporting stage 31 is moved reciprocatingly and horizontally along the guide shafts 36, 37 by means of a motor 32 (shown in FIG. 5), pulleys 33, 34 (shown in FIG. 1) and a timing belt 35. When the test strip-receiving groove 38 formed on the stage 31 receives a test strip falling through the test strip-conducting opening 20 formed in the container-supporting table 18, the stage 31 transports the test strip to the external take-out position A. A portion under the test strip-receiving groove 38 is provided with a heads-or-tails detector 40 (shown in FIG. 2) which optically distinguishes between heads and tails of a test strip placed in the groove 38. Side-reversing means 44 is provided facing the moving path of the carrying stage 31. The side-reversing means 44 is composed of a driving motor 43 (shown in FIG. 5) and a rotational member 42 having a slit-like groove 41. If the reagent sections 9 of a test strip 14 are face down, the test strip is flipped over by the side-reversing means 44, which rotates the rotational member 42 substantially 180° when a handle portion of the facing-down test strip 14 comes into the slit-like groove 41 of the rotational member 42. The shutter 45 (shown in FIGS. 1 and 2) is operated by a solenoid 46 to open and close the test strip-conducting opening 20 of the container-supporting table 18. A detector 47 and a detection terminal 48 are provided for determining the position where the transporting stage 31 is stopped.

According to this embodiment, the cylindrical container 11 has a capacity for 200 test strips, and test strips are placed in the container 11, with the handle portions of the test strips being closer to the bottom (the right side wall in FIG. 4) of the container 11. The operation of the device according to this embodiment is initiated in the state shown in FIG. 1, where the container 11 is mounted and the opening 20 of the container-supporting table 18 is closed by the shutter 45, and proceeds as follows.

(1) The pulse motor 25 is operated to reciprocally rotate the cylindrical container 11 several times so that a test strip slips into the slit 15. According to this embodiment, a test strip slips into the slit 15 substantially without fail by rotating the container to 75° back and forth four times. A detector 49 is provided for confirming that a test strip is fitted in the slit 15.

(2) When the slit 15 of the container 11 directly faces the opening 20, the opening 20 of the container-supporting table 18 is opened by forcing down the shutter 45, thus allowing the test strip in the slit 15 to fall trough the opening 20. In this procedure, another test strip sometimes immediately follows a falling test strip.

Figure 2:
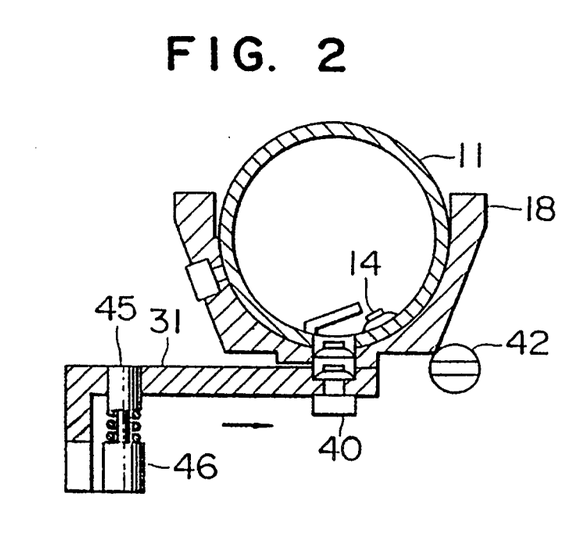
FIG. 2 illustrates the operation of the device shown in FIG. 1, FIG. 3 further illustrates the operation of the device shown in FIG. 1.

(3) The transporting stage 31 is moved backward (to the left in FIG. 1) until the test strip-receiving groove 38 takes a position under the opening 20, so that the falling test strip is received and fitted in the groove 38 (see FIG. 2).

(4) The transporting stage 31 is moved forward (in the direction indicated by the arrow in FIG. 2) in order to transport the test strip to the external take-out position A. A test strip which comes down immediately following another test strip is stopped in the opening 20 or in an exit by a barrier 50 (shown in FIG. 3) which is provided diagonally under the opening 20 for stopping such a test strip.

(5) While the test strip is being transported, it is found out whether the test strip is faced up or down by the heads-or-tails detector 40. If face down, the test strip is flipped over so as to face up by the side-reversing means 44 (see FIG. 3).

Figure 3:
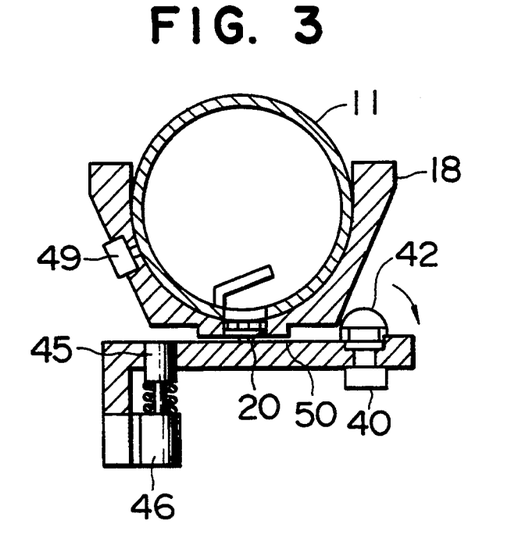

(6) When the test strip is brought to the external take-out position A, the shutter means is returned to a position corresponding to the opening 20, and the solenoid 46 is actuated to push the test strip remaining in the opening or in the exit, back into the container 11, and then the opening 20 is closed. In order to take out the next test strip, the operation goes back to (1) and is repeated.

By repeating the above-described procedure, the test strips contained in the cylindrical container 11 are continuously and automatically sent out to the test strip supply position. If the test strip automatic supply device of this embodiment is employed in an automatic analytical instrument for urine, test strips can be supplied at a rate of one strip per 12 seconds.

Although the functions of the test strip's heads-or-tails detector and the side-reversing means are important in the above-described embodiment, the schemes and methods thereof are not limited to those described above. For example, instead of providing such device and means in a test strip automatic supply device, the test strip's side-reversing function may be incorporated into robot mechanism for transporting test strips from a supply position to an analyzing unit. Further, though the drying agent chamber is provided in the inner side of the closure of the container in the above embodiment, the position and shape thereof are not limited to those described above. For example, a drying agent chamber may be provided on the inside surface of the container body.

Since a test strip automatic supply device according to the present invention automatically and smoothly supplies elongate test strips, the device significantly will improve the operability of a test strip automatic analytical instrument if the device is employed therein.

What is claimed is:

1. A test strip automatic supply method for a test strip analytical instrument, comprising the steps of:
   providing a test strip automatic supply device having a cylindrical container containing a plurality of test strips, a wall having a slit therein, an opening adjacent the slit, and an external take-out position;
   reciprocally rotating the cylindrical container to fit one of the test strips into the slit so that a longitudinal direction of the test strip is parallel to a rotation axis of said container;
   closing the opening so as to prevent the test strip from entering the opening during rotation of said container;
   passing the test strip fitted into said slit out of said container via said slit and through said opening when rotation of the container is stopped;
   positioning said test strip at an external take-out position of the test strip automatic supply device; and
   transporting the test strip positioned at the external take-out position to a test strip dipping position for contact with a sample to be analyzed.

2. A test strip automatic supply method according to claim 1, wherein said container is rotated to 30° or greater both clockwise and counterclockwise during said reciprocally rotating step.

3. A test strip analytical instrument, comprising:
   a test strip automatic supply device comprising a rotatable cylindrical test strip container for holding a plurality of test strips and having a wall and a slit therein through which a test strip is passed;
   driving means for reciprocally rotationally driving said test strip container through a predetermined angle;
   means, arranged along the wall of said test strip container, for preventing any test strip from spilling out through said container slit during rotation of said test strip container, including an opening for passing a test strip fitted in said container slit when said rotation stops;
   a test strip transporting stage which has a groove for receiving the test strip having passed through said container slit and which moves so that said groove moves between a position at which the test strip is received from said container slit and an external take-out position;
   means for closing the opening of said preventing means so as to prevent any test strip from entering into the opening during rotation of said container, said closing means allowing a test strip to pass through said opening when the rotation is stopped; and
   means for transporting the test strip from the take-out position to a test strip dipping position at which the test strip contacts a sample to be analyzed.

4. A test strip automatic supply device according to claim 3, wherein said spill-out preventing means is placed between said test strip container and said test strip transporting stage.

5. A test strip automatic supply device according to claim 3, further comprising:
   means for detecting an obverse portion or a reverse portion of the test strip received in said groove on said test strip transporting stage;
   a rotational member having a slit into which an end portion of a test strip fits; and
   a rotational member driving means for rotating said rotational member substantially 180° so as to flip over the test strip when the reverse portion of the detected test strip is placed in a state of facing up;
   wherein the transporting stage transports a test strip horizontally, the end portion of said test strip being inserted into the slit of said rotational member during said horizontal transport.

6. A test strip analytical instrument, comprising:
   (a) a rotatable cylindrical test strip container for holding a plurality of test strips, said container having a peripheral wall;
   (b) a slit formed in the peripheral wall and capable of fitting one of the test strips therein, said slit being located to make a longitudinal direction thereof substantially parallel to a rotation axis of said container;
   (c) a guide member for directing any one of the test strips in said container along said slit and guiding said test strip to said slit;
   (d) driving means for reciprocally and rotationally driving said container through a predetermined angle;

(e) means for preventing the test strip from spilling out through said slit during rotation of said container, said preventing means being arranged along the peripheral wall of said container and having an opening for passing the test strip fitted in said slit therethrough when rotation of said container is paused;

(f) a test strip transporting stage having a groove for receiving the test strip fitted in said slit through the opening of said preventing means, said transporting means transporting the test strip received in the groove to a take-out position;

(g) means for closing the opening of said preventing means so as to prevent any test strip from entering into the opening thereof during rotation of said container, said closing means allowing the test strip fitted in said slit to pass through said opening thereof when the rotation of said container is paused; and (h) means for transporting the test strip from the take-out position to a contacting position where a sample to be analyzed is put in contact with the test strip.

7. A test strip automatic supply device according to claim 6, wherein said test strip container has an opening at an end of the container and a closure for covering the opening.

8. A test strip automatic supply device according to claim 6, wherein said test strip container comprises a test strip-containing chamber having a depth that is at least as great as a length of the plurality of test strips contained therein, and a drying agent chamber for containing a drying agent.

9. A test strip automatic supply device according to claim 6, wherein a clearance between said guide member and an upper edge of said slit is greater than a height of the test strip but smaller than twice the height of the test strip.

10. A test strip automatic supply device according to claim 6, wherein said driving means includes torque transmitting means for rotationally driving said test strip container, and said test strip container is detachably supported by said torque transmitting means.

11. A test strip analytical instrument comprising:

a test strip automatic supply device including a rotatable container having a wall and a slit in the wall into which a test strip is fitted, said slit being oriented so that a longitudinal direction thereof extends substantially parallel to a revolution axis of said container, a guide member for directing the test strip along said slit and guiding the test strip to said slit, and transporting means for receiving the test strip fitted in said slit of said container and for transporting said test strip to an external take-out position;

means for preventing the test strip fitted in said slit from spilling out through said slit during rotation of said container, said preventing means being arranged along the wall of said container and having an opening for passing the test strip fitted in said slit therethrough when rotation of said container is paused;

means for closing the opening of said preventing means so as to prevent a test strip from entering into the opening thereof during rotation of said container, said closing means allowing a test strip to pass through said opening thereof when the rotation of said container is paused; and test strip handling means which has a grip device for gripping a test strip supplied to the external take-out position, transporting said test strip to a test strip dipping position, dipping said test strip gripped by said grip device into a sample at the test strip dipping position, transporting the test strip to a measuring device, releasing said test strip at the measuring device, and returning said grip device to the external take-out position, wherein said test strip automatic supply device supplies a second test strip to the external take-out position after said grip device grips a first test strip and before said grip device is returned to the external take-out position.

* * * * *